US008450560B2

(12) United States Patent
Fukusaki et al.

(10) Patent No.: US 8,450,560 B2
(45) Date of Patent: May 28, 2013

(54) **GENE CLUSTER OF PRENYL TRANSFERASE FROM *HEVEA BRASILIENSIS***

(75) Inventors: Eiichiro Fukusaki, Suita (JP); Tomoki Sando, Kodaira (JP); Norie Watanabe, Higashimurayama (JP); Akio Kobayashi, Osaka (JP); Nadirman Haska, Jakarta (ID)

(73) Assignee: Bridgestone Corporation, Tokyo (JP)

( * ) Notice: Subject to any disclaimer, the term of this patent is extended or adjusted under 35 U.S.C. 154(b) by 200 days.

(21) Appl. No.: 12/696,367

(22) Filed: Jan. 29, 2010

(65) Prior Publication Data
US 2010/0186111 A1 Jul. 22, 2010

Related U.S. Application Data (62) Division of application No. 11/522,390, filed on Sep. 18, 2006, now Pat. No. 7,692,066.

(30) Foreign Application Priority Data

Sep. 16, 2005 (JP) .................................. 2005-269829
Sep. 4, 2006 (JP) .................................. 2006-238745

(51) Int. Cl.
*C12N 9/00* (2006.01)
*C12N 15/29* (2006.01)
*C12N 15/52* (2006.01)
*C12N 15/82* (2006.01)

(52) U.S. Cl.
USPC ....... 800/284; 435/183; 435/320.1; 536/23.2; 536/23.6; 800/298

(58) Field of Classification Search
USPC .................................................. 800/278, 298
See application file for complete search history.

(56) References Cited

FOREIGN PATENT DOCUMENTS

| EP | 0 674 000 A3 | 9/1995 |
| EP | 0 974 661 A1 | 1/2000 |
| WO | WO 00/28005 A1 | 5/2000 |
| WO | WO 01/29188 A1 | 4/2001 |
| WO | WO 2004/011667 A3 | 2/2004 |

OTHER PUBLICATIONS

Souza Goncalves, P. et al. Rev. Brasil. Genet. (1985) VIII, 2 pp. 319-327.*
Indonesian Office Action for Application No. P-00 2006 00545 dated Jul. 6, 2011.
Takaya et al., "Cloning, expression and characterization of a functional cDNA clone encoding geranylgeranyl diphospate synthase of *Hevea brasiliensis*", *Biochimica et Biophysica Acta*, 1625:214-220 (2003).
Kim et al., "Isolation of a cDNA encoding geranylgeranyl diphosphate synthase from citrus" (GenBank AY166797), Dec. 19, 2002.
Japanese Office Action issued Jan. 24, 2012, for corresponding Japanese Application No. 2006-238745.

(Continued)

*Primary Examiner* — Russell Kallis
(74) *Attorney, Agent, or Firm* — Sughrue Mion, PLLC (57) ABSTRACT

According to the present invention, a gene cluster encoding various kinds of prenyl transferase of *Hevea brasiliensis* is obtained, and the nucleotide sequences of these genes are determined. The prenyl transferases are involved in the biosynthesis of isoprene backbone of natural rubber. Therefore, improvement of productivity of rubber can be expected, by transforming plants by the gene cluster obtained in the present invention.

6 Claims, 1 Drawing Sheet

OTHER PUBLICATIONS

Cornish et al., "Effect of Different Allylic Diaphosphates on the Initiation of New Rubber Molecules and on Cis-1,4-polyisoprene Biosynthesis in Guayule (*Parthenium argentatum* Gray)", J. Plant. Physiol., 147:301-305 (1995), XP 55044715.

Light et al., "Purification of a Prenyltransferase that Elongates *cis*-Polyisoprene Rubber from the Latex of *Hevea Brasiliensis*", Journal of Biological Chemistry, 264(31):18589-18597 (1989).

Dennis et al., "Rubber Enlongation Factor from *Hevea Brasiliensis*", Journal of Biological Chemistry, 264(31):18608-18617 (1989).

Cornish et al., "Biochemistry of natural rubber, a vital raw material, emphasizing Biosynthetic rate, molecular weight and compartmentalization, in evolutionarily divergent plant species", Nat. Prod. Rep., 18:182-189 (2001).

French Search Report for Application No. 0608145 dated Dec. 3, 2012, with a Written Opinion and Partial English Translation.

* cited by examiner

SEQUENCE LISTING

```
<160> NUMBER OF SEQ ID NOS: 8

<210> SEQ ID NO 1
<211> LENGTH: 1074
<212> TYPE: DNA
<213> ORGANISM: Hevea brasiliensis

<400> SEQUENCE: 1
agtaaagaaa gagactatag gaatctttag atttgaattt tcattttct tccccaagat      60 ataccttccc aatctcaaca acagccacgt ttttctcctc cttctcctcc tgtacaacac     120
cacccatggc cggagctctc tcttctacca tacatggaaa tctcatagct cgtgctgtct     180
ccagttccaa tcctaaacac ccattattct ctcatagacc catggtagtt gccatgtcca     240
ctgaccagtc ttattggagc tctgtcaatg ctgacctcga cacacatctc aagcaagcca     300
ttcccataag gcaaccgctc gcggtctttg agcccatgcg ccatctcatc ttatccgccc     360
cacaaacttc cgcacccgcc ttgtgtatcg ccgcttgtga actcgttggt ggccaccgga     420
accaagccat ggctgcagca tccgctttac gtctcgtgca tgcttctgct tccactcatg     480
agaacctgcc tttgacagac aggcccaggc cgatgcccag aaccaggccc actttatatg     540
gccctaacat cgagcttctc atagcagatg gaataatacc atacgggttt gagttactgg     600
cacgggacga cgacgctgcc gaaaataatt cgaatcgggt tttgcgtgct atcattgaga     660
tctcacgtgc catgggttca caaggagtga tcgaagggca atataatgaa tcacaatacg     720
aggaatcgga gggggaggaa atattccacg tgggatggct tcaaaatgta tgtagaaaaa     780
```

```
aagaaggtac cttacacgcg tgtgcgggtg cgtgtggcgc aatattagga ggtggaagcg    840
aagacgagat agaaaaattg agaaggtatg gcttgtatgt aggaatggta caaggaatat    900
tgagcaaggt tgatgaaagg aaggagtggc cagtgaaaga ggtgaataag ctaagagatt    960
tggctcttaa agaattgaaa gatttcaacc aagcaaggt taaaacaatt tctatccttg    1020
ttgagaccag gttttgtaat ttatgagttt tacaagatca aaaaaaaaaa aaaa          1074
```

```
<210> SEQ ID NO 2
<211> LENGTH: 306
<212> TYPE: PRT
<213> ORGANISM: Hevea brasiliensis

<400> SEQUENCE: 2

Met Ala Gly Ala Leu Ser Ser Thr Ile His Gly Asn Leu Ile Ala Arg
1               5                   10                  15

Ala Val Ser Ser Asn Pro Lys His Pro Leu Phe Ser His Arg Pro
            20                  25                  30

Met Val Ala Met Ser Thr Asp Gln Ser Tyr Trp Ser Val Asn
        35                  40                  45

Ala Asp Leu Asp Thr His Leu Lys Gln Ala Ile Pro Ile Arg Gln Pro
50                  55                  60

Leu Ala Val Phe Glu Pro Met Arg His Leu Ile Leu Ser Ala Pro Gln
65                  70                  75                  80

Thr Ser Ala Pro Ala Leu Cys Ile Ala Ala Cys Glu Leu Val Gly Gly
                85                  90                  95

His Arg Asn Gln Ala Met Ala Ala Ser Ala Leu Arg Leu Val His
            100                 105                 110

Ala Ser Ala Ser Thr His Glu Asn Leu Pro Leu Thr Asp Arg Pro Arg
        115                 120                 125

Pro Met Pro Arg Thr Arg Pro Thr Leu Tyr Gly Pro Asn Ile Glu Leu
    130                 135                 140

Leu Ile Ala Asp Gly Ile Ile Pro Tyr Gly Phe Glu Leu Leu Ala Arg
145                 150                 155                 160

Asp Asp Asp Ala Ala Glu Asn Asn Ser Asn Arg Val Leu Arg Ala Ile
                165                 170                 175

Ile Glu Ile Ser Arg Ala Met Gly Ser Gln Gly Val Ile Glu Gly Gln
            180                 185                 190

Tyr Asn Glu Ser Gln Tyr Glu Glu Ser Glu Gly Glu Ile Phe His
        195                 200                 205

Val Gly Trp Leu Gln Asn Val Cys Arg Lys Lys Glu Gly Thr Leu His
    210                 215                 220

Ala Cys Ala Gly Ala Cys Gly Ala Ile Leu Gly Gly Ser Glu Asp
225                 230                 235                 240

Glu Ile Glu Lys Leu Arg Arg Tyr Gly Leu Tyr Val Gly Met Val Gln
                245                 250                 255

Gly Ile Leu Ser Lys Val Asp Glu Arg Lys Glu Trp Pro Val Lys Glu
            260                 265                 270

Val Asn Lys Leu Arg Asp Leu Ala Leu Lys Glu Leu Lys Asp Phe Asn
        275                 280                 285

Gln Ala Lys Val Lys Thr Ile Ser Ile Leu Val Glu Thr Arg Phe Cys
    290                 295                 300

Asn Leu
305

<210> SEQ ID NO 3
```

```
<211> LENGTH: 1662
<212> TYPE: DNA
<213> ORGANISM: Hevea brasiliensis

<400> SEQUENCE: 3
agctatatag actcatatag ggaattcctt agatttgaga gaatctccaa gaatggtttc      60
tctttggtta tatcaccatc acctgccctc ttccttccaa gaaaacttcc taatcttcgc     120
cgctccaaac ctccactatc aattcactct tctgcttctt cttcttcttc ttctatttct     180
atgtccgttt caggcaattc gaaatcgacc cagttcgatt tgaagactta ttggatgact     240
cttatatcag agatcaacca gaagcttgat caggctattc cgattcaata cccagaggag     300
atctatgagg ccatgagata ttccgtgctc gcaaagcgga ccaagcgagc ccgcctgtc      360
atgtgtattc ctgcctgtga gctcttcggt ggtaatcgcc tcgctgcctt ccctactgca     420
tgtgctcttg aaatggtcca tgcagcttct ttgattcatg atgatcttcc ctgcatggat     480
gatgccccat cacgtcgagg ccagccctca aaccatgcag tctatggggt tgacaaggca     540
atccttgctg gggatgcact gttccctctt ggcttccgac acattgtctc caacacaccc     600
tcagatcttg ttccagagcc tcgccttctc cgtgtgattg ctgagattgc tcgtgctgtg     660
gggtccacgg gaatggctgc tggtcagttc cttgacctcg agggtagcct aaattctgca     720
gagtttgttc aagagaaaaa atatggtgaa atgggtgagt gttctgcagt gtgcggagga     780
ttgttggctg gtgctgaaga tgatgagata caaagattga ggaggtatgg aagagctgtt     840
ggggtattat ataaagtgat tgatgatgta ttggaagcaa atcaatgag taaggaagat     900
gaggagaatg agaaaaagaa agcgaaaagt tatgtcagtt tatatggggt tgagaaggca     960
gtggaggttg cagaagagct gagaaccaag gctaagaagg aattggatgg gtttgagaag    1020
tatggggaga gtgtccagcc actatataac tttgttgatt atgcagctga tagaggtttc    1080
agtgttttag agttgaattg atgatggtgt tttaggtcct attctggtgg agaatctta    1140
tatttaggag taactatgg attggatgga tggaaagtat ggcataccac cattggcatt    1200
aatattttga tggttcatca tgctgttgca ggtgaagttc ttataactgt agttgaattc    1260
tactggtttt cctcccttgg cttttcggct acaaaaatcc cagatggtgg caaggacgat    1320
gagataacga cagcaacctt tgtgtgattt cccatatga atgttcggtt aagacttctc    1380
agggtccaag tttgataggt cttgcaccat ttcccttacg ggaaagtgct ttcgctgatt    1440
acgtaaattg aagttgttgt gtcgatcaat aatttgggtg aggaaacaag gagatagaaa    1500
ggacaagccg cattagtaaa gatgacatat cattagcttt cccgtgtatt caattgaaga    1560
cgatcatgta ttgccttgtt tattggctcg aaaattatgc attatttaga ttgggggata    1620
atggatcctt tattgcaaga ttgctaaaaa aaaaaaaaaa aa                       1662

<210> SEQ ID NO 4
<211> LENGTH: 306
<212> TYPE: PRT
<213> ORGANISM: Hevea brasiliensis

<400> SEQUENCE: 4

Met Ser Val Ser Gly Asn Ser Lys Ser Thr Gln Phe Asp Leu Lys Thr
1               5                   10                  15

Tyr Trp Met Thr Leu Ile Ser Glu Ile Asn Gln Lys Leu Asp Gln Ala
            20                  25                  30

Ile Pro Ile Gln Tyr Pro Glu Glu Ile Tyr Glu Ala Met Arg Tyr Ser
        35                  40                  45

Val Leu Ala Lys Arg Thr Lys Arg Ala Pro Pro Val Met Cys Ile Ala
```

```
                50                  55                  60
Ala Cys Glu Leu Phe Gly Gly Asn Arg Leu Ala Phe Pro Thr Ala
 65                  70                  75                  80

Cys Ala Leu Glu Met Val His Ala Ala Ser Leu Ile His Asp Asp Leu
                 85                  90                  95

Pro Cys Met Asp Asp Ala Pro Ser Arg Arg Gly Gln Pro Ser Asn His
                100                 105                 110

Ala Val Tyr Gly Val Asp Lys Ala Ile Leu Ala Gly Asp Ala Leu Phe
            115                 120                 125

Pro Leu Gly Phe Arg His Ile Val Ser Asn Thr Pro Ser Asp Leu Val
            130                 135                 140

Pro Glu Pro Arg Leu Leu Arg Val Ile Ala Glu Ile Ala Arg Ala Val
145                 150                 155                 160

Gly Ser Thr Gly Met Ala Ala Gly Gln Phe Leu Asp Leu Glu Gly Ser
                165                 170                 175

Leu Asn Ser Ala Glu Phe Val Gln Glu Lys Lys Tyr Gly Glu Met Gly
            180                 185                 190

Glu Cys Ser Ala Val Cys Gly Gly Leu Leu Ala Gly Ala Glu Asp Asp
            195                 200                 205

Glu Ile Gln Arg Leu Arg Arg Tyr Gly Arg Ala Val Gly Val Leu Tyr
210                 215                 220

Lys Val Ile Asp Asp Val Leu Glu Ala Lys Ser Met Ser Lys Glu Asp
225                 230                 235                 240

Glu Glu Asn Glu Lys Lys Lys Ala Lys Ser Tyr Val Ser Leu Tyr Gly
                245                 250                 255

Val Glu Lys Ala Val Glu Val Ala Glu Glu Leu Arg Thr Lys Ala Lys
            260                 265                 270

Lys Glu Leu Asp Gly Phe Glu Lys Tyr Gly Glu Ser Val Gln Pro Leu
            275                 280                 285

Tyr Asn Phe Val Asp Tyr Ala Ala Asp Arg Gly Phe Ser Val Leu Glu
            290                 295                 300

Leu Asn
305

<210> SEQ ID NO 5
<211> LENGTH: 1278
<212> TYPE: DNA
<213> ORGANISM: Hevea brasiliensis

<400> SEQUENCE: 5
tctctctttc tgcttcgctt ctcgaggagc tgcaataaga aagactagca gctatgcaat    60
tcttgcggtg tgtctctcag atttcgagaa acggccgtcg tttgtttctc tctcgtcaat   120
tagacccgtt tcttatatca aatagttccc aacttcttgg agactctact cataaggtct   180
tcaatcgcag agaaactttt tcttggagtt tttctgccct gcatggcttc aaacagcaaa   240
ttcatcacca gagcagttcc ttgattgagg agccacttga tccgttctca cttgttgctg   300
atgaactatc actccttgct aataggttac gggctatggt agttgctgag gttcctaagc   360
ttgcctcagc tgctgaatac ttcttcaaaa tgggagtaga aggaaagagg tttcgtccca   420
cggtattgtt gctgatggct acagctttaa atgtgcacat acatgaacct atgccaaatg   480
gtgttggaga cactttgggt gcggaactgc gtacgagaca gcaatgcata gctgaaatta   540
cagaaatgat ccatgtggca agtctcctcc atgatgatgt tctggatgat gcagacacta   600
gacgtggtat tggttcttta aattttgtca tgggcaataa ggtagcagta ttagcagggg   660
```

```
attttctgct tcacgagct tgtgtagccc ttgcttcttt gaaaaacacc gaggttgttt     720 cactttagc gacagttgta gagcatcttg tgacaggtga aaccatgcag atgactagta     780
catcagagca acgttgtagc atggatcact atatgcaaaa gacatactac aagactgcat    840
ctttgatttc aaacagctgc aaagccattg ccctccttgc tgggcaaaca acagaagttg    900
caatgttggc ttttgagtat ggcaaaaatc tgggattggc atttcagttg atagatgatg    960
tccttgattt cacaggcaca tctgcttcac ttggaaaggg ttcattatcc gacattcgac    1020
atgtaatccg tctatccctg atatgatatc tgaatgatgg aaatactaga tggtttttaa    1080
cttctaagct ctcattggat atggtcaaca ggcttgtcga aggaaaaaaa aatattattt    1140
ttgcattttc agtgagcatt tcatttgta taagccaaaa ctgaagcaac tttgcttact     1200
catccaaaca ctctatttgg aaaagttagt atgatgaatt caattcaatt tggatgattg    1260
gttccaaaaa aaaaaaaa                                                  1278

<210> SEQ ID NO 6
<211> LENGTH: 330
<212> TYPE: PRT
<213> ORGANISM: Hevea brasiliensis

<400> SEQUENCE: 6

Met Gln Phe Leu Arg Cys Val Ser Gln Ile Ser Arg Asn Gly Arg Arg
1               5                   10                  15

Leu Phe Leu Ser Arg Gln Leu Asp Pro Phe Leu Ile Ser Asn Ser Ser
                20                  25                  30

Gln Leu Leu Gly Asp Ser Thr His Lys Val Phe Asn Arg Arg Glu Thr
            35                  40                  45

Phe Ser Trp Ser Phe Ser Ala Leu His Gly Phe Lys Gln Gln Ile His
        50                  55                  60

His Gln Ser Ser Leu Ile Glu Glu Pro Leu Asp Pro Phe Ser Leu
65                  70                  75                  80

Val Ala Asp Glu Leu Ser Leu Leu Ala Asn Arg Leu Arg Ala Met Val
                85                  90                  95

Val Ala Glu Val Pro Lys Leu Ala Ser Ala Glu Tyr Phe Phe Lys
            100                 105                 110

Met Gly Val Glu Gly Lys Arg Phe Arg Pro Thr Val Leu Leu Leu Met
        115                 120                 125

Ala Thr Ala Leu Asn Val His Ile His Glu Pro Met Pro Asn Gly Val
130                 135                 140

Gly Asp Thr Leu Gly Ala Glu Leu Arg Thr Arg Gln Gln Cys Ile Ala
                145                 150                 155                 160

Glu Ile Thr Glu Met Ile His Val Ala Ser Leu Leu His Asp Asp Val
            165                 170                 175

Leu Asp Asp Ala Asp Thr Arg Arg Gly Ile Gly Ser Leu Asn Phe Val
        180                 185                 190

Met Gly Asn Lys Val Ala Val Leu Ala Gly Asp Phe Leu Leu Ser Arg
    195                 200                 205

Ala Cys Val Ala Leu Ala Ser Leu Lys Asn Thr Glu Val Val Ser Leu
210                 215                 220

Leu Ala Thr Val Val Glu His Leu Val Thr Gly Glu Thr Met Gln Met
225                 230                 235                 240

Thr Ser Thr Ser Glu Gln Arg Cys Ser Met Asp His Tyr Met Gln Lys
                245                 250                 255

Thr Tyr Tyr Lys Thr Ala Ser Leu Ile Ser Asn Ser Cys Lys Ala Ile
            260                 265                 270
```

Ala Leu Leu Ala Gly Gln Thr Thr Glu Val Ala Met Leu Ala Phe Glu
            275                 280                 285

Tyr Gly Lys Asn Leu Gly Leu Ala Phe Gln Leu Ile Asp Asp Val Leu
        290                 295                 300

Asp Phe Thr Gly Thr Ser Ala Ser Leu Gly Lys Gly Ser Leu Ser Asp
305                 310                 315                 320

Ile Arg His Val Ile Arg Leu Ser Leu Ile
            325                 330

<210> SEQ ID NO 7
<211> LENGTH: 1181
<212> TYPE: DNA
<213> ORGANISM: Hevea brasiliensis

<400> SEQUENCE: 7

```
tctctctttc tgcttcgctt ctcgaggagc tgcaataaga aagactagca gctatgcaat      60
tcttgcgggg tttatcaccg atttcgagaa gcggcctccg cttgtttctt tctcgtcaac     120
tatacccgtt ccctgtcgcc aatagttccc agcttcttgg agactctact cagaaggtct     180
ttaatcgcag agaaacttat tcctggagtt tagttgactc gcatggcttc aaacagcaaa     240
ttcatcatca aagcagtttc ttgagtgagg agccactcga cccgttctct cttgttgctg     300
atgagctatc acttgttgct aataggttgc gggctatgct agtttccgag gttcctaagc     360
ttgcctcagc tgctgaatac ttcttcaaaa tgggagtaga aggaaagagg cttcgtccca     420
cagttttgtt gctgatggct acagctttaa atgtgcacat acctgaacaa attgttggag     480
acactttggc tgcagaactg cgtacgagac agcaatgcat agctgaaatt acagaaatga     540
tacatgtggc gagtctcctc cacgatgatg tgctagatga tgcagaaact agacgcagta     600
tcagttcatt aaattttgtc atgggcaata aggtagcagt gttagctgga gattttctgc     660
tttcgcgagc ttgtgtagcc gttgcatctt tgaaaaacac tgaggttgtt tcactgctag     720
cgatagctgt agagcatctt gtgactggtg aaaccatgca gatgacttgc acatctgagc     780
aacgttgtag catggagtac tatatgaaaa agacatacta caagactgca tcttttgatct    840
caaacagctg caaagcaatt gcccttcttg ctgggcaaac cacagaagtt gcaacgttgg     900
cttttgagta tggcaaaaat ctgggattgg catttcagtt gatagatgac gtccttgatt     960
tcacaggcac atttgcttca cttggaaagg gttcattgtc tgacattcgc catgtaatcc    1020
ctgatgtgat atctgaatga cgggattttt tttaacttt aagctctcat tatttatgag     1080
atgtggtcaa caagcttgtt atatactttt gctttatttt tgttggagga aagaaattat    1140
tactttggca ttttcaaaaa aaaaaaacaa aaaaaaaaa a                         1181
```

<210> SEQ ID NO 8
<211> LENGTH: 328
<212> TYPE: PRT
<213> ORGANISM: Hevea brasiliensis

<400> SEQUENCE: 8

Met Gln Phe Leu Arg Gly Leu Ser Pro Ile Ser Arg Ser Gly Leu Arg
1               5                   10                  15

Leu Phe Leu Ser Arg Gln Leu Tyr Pro Phe Pro Val Ala Asn Ser Ser
            20                  25                  30

Gln Leu Leu Gly Asp Ser Thr Gln Lys Val Phe Asn Arg Arg Glu Thr
        35                  40                  45

Tyr Ser Trp Ser Leu Val Asp Ser His Gly Phe Lys Gln Gln Ile His
    50                  55                  60

```
His Gln Ser Ser Phe Leu Ser Glu Pro Leu Asp Pro Phe Ser Leu
 65                  70                  75                  80

Val Ala Asp Glu Leu Ser Leu Val Ala Asn Arg Leu Arg Ala Met Leu
             85                  90                  95

Val Ser Glu Val Pro Lys Leu Ala Ser Ala Ala Glu Tyr Phe Phe Lys
            100                 105                 110

Met Gly Val Glu Gly Lys Arg Leu Arg Pro Thr Val Leu Leu Leu Met
            115                 120                 125

Ala Thr Ala Leu Asn Val His Ile Pro Glu Gln Ile Val Gly Asp Thr
            130                 135                 140

Leu Ala Ala Glu Leu Arg Thr Arg Gln Gln Cys Ile Ala Glu Ile Thr
145                 150                 155                 160

Glu Met Ile His Val Ala Ser Leu Leu His Asp Asp Val Leu Asp Asp
                165                 170                 175

Ala Glu Thr Arg Arg Ser Ile Ser Ser Leu Asn Phe Val Met Gly Asn
                180                 185                 190

Lys Val Ala Val Leu Ala Gly Asp Phe Leu Leu Ser Arg Ala Cys Val
            195                 200                 205

Ala Val Ala Ser Leu Lys Asn Thr Glu Val Val Ser Leu Leu Ala Ile
            210                 215                 220

Ala Val Glu His Leu Val Thr Gly Glu Thr Met Gln Met Thr Cys Thr
225                 230                 235                 240

Ser Glu Gln Arg Cys Ser Met Glu Tyr Tyr Met Lys Lys Thr Tyr Tyr
                245                 250                 255

Lys Thr Ala Ser Leu Ile Ser Asn Ser Cys Lys Ala Ile Ala Leu Leu
                260                 265                 270

Ala Gly Gln Thr Thr Glu Val Ala Thr Leu Ala Phe Glu Tyr Gly Lys
            275                 280                 285

Asn Leu Gly Leu Ala Phe Gln Leu Ile Asp Asp Val Leu Asp Phe Thr
            290                 295                 300

Gly Thr Phe Ala Ser Leu Gly Lys Gly Ser Leu Ser Asp Ile Arg His
305                 310                 315                 320

Val Ile Pro Asp Val Ile Ser Glu
                325
```

GENE CLUSTER OF PRENYL TRANSFERASE FROM *HEVEA BRASILIENSIS*

This application is a Divisional of U.S. application Ser. No. 11/522,390, filed Sep. 18, 2006 (now allowed); which claims priority under 35 U.S.C. §365(b) from JP 2005-269829, filed Sep. 16, 2005, and JP 2006-238745, filed Sep. 4, 2006; the entire disclosure of each of which is incorporated herein by reference.

BACKGROUND OF THE INVENTION

1. Field of the Invention

This invention relates to a cluster of prenyl transferase from *Hevea brasiliensis* and a gene cluster encoding said enzyme.

2. Related Art

So far, genes of isopentenyl disphosphate isomerase (IPP isomerase), farnesyl disphosphate synthase, trans-type short chaine prenyl disphosphate synthase of geranylgeranyl disphosphate synthase and cis-type prenyl disphosphate synthase have been isolated from *Hevea brasiliensis*, and functional analysis of the enzymes encoded by these genes has been performed. As to some trans-type prenyl disphosphate synthases derived from animals and prokaryotes, the correlation between the amino acid sequence and the carbon length of the product (trans-prenyl diphosphate) has been elucidated.

As to known documents that have been published in the past, such documents include patent application related to IPP isomerase of *Hevea brasiliensis* (Japanese Patent Publication No. 2000-200276), academic document about cloning of IPP isomerase from *Hevea brasiliensis* (Soo Kyung Oh et al., J. Plant Physiol. 157(2000) 549-557), academic document about cloning of geranylgeranyl diphosphate synthase from *Hevea brasiliensis* (A. Takaya et al., Biochimica et Biophysica Acta 1625(2003)214-220), and academic document about cloning of cis-prenyl transferase from *Hevea brasiliensis* (K. Asawatreratanaku Eur. J. Biochem. 270(2003) 4671-4680).

The enzyme, which function to catalyze ligating isopentenyl diphosphate (IPP) with allyl substrate sequentially, is generally referred to prenyl transferase, because it ligates isoprene unit sequentially. In addition, the term prenyl transferase generally means a concept of the enzyme catalyzing condensation reaction between IPP and an isoprenyl diphosphate (C5n) (allyl substrate) and synthesizing new an isoprenyl diphosphate (C5n+1) in which one more isoprene unit is increased.

Figure 1:
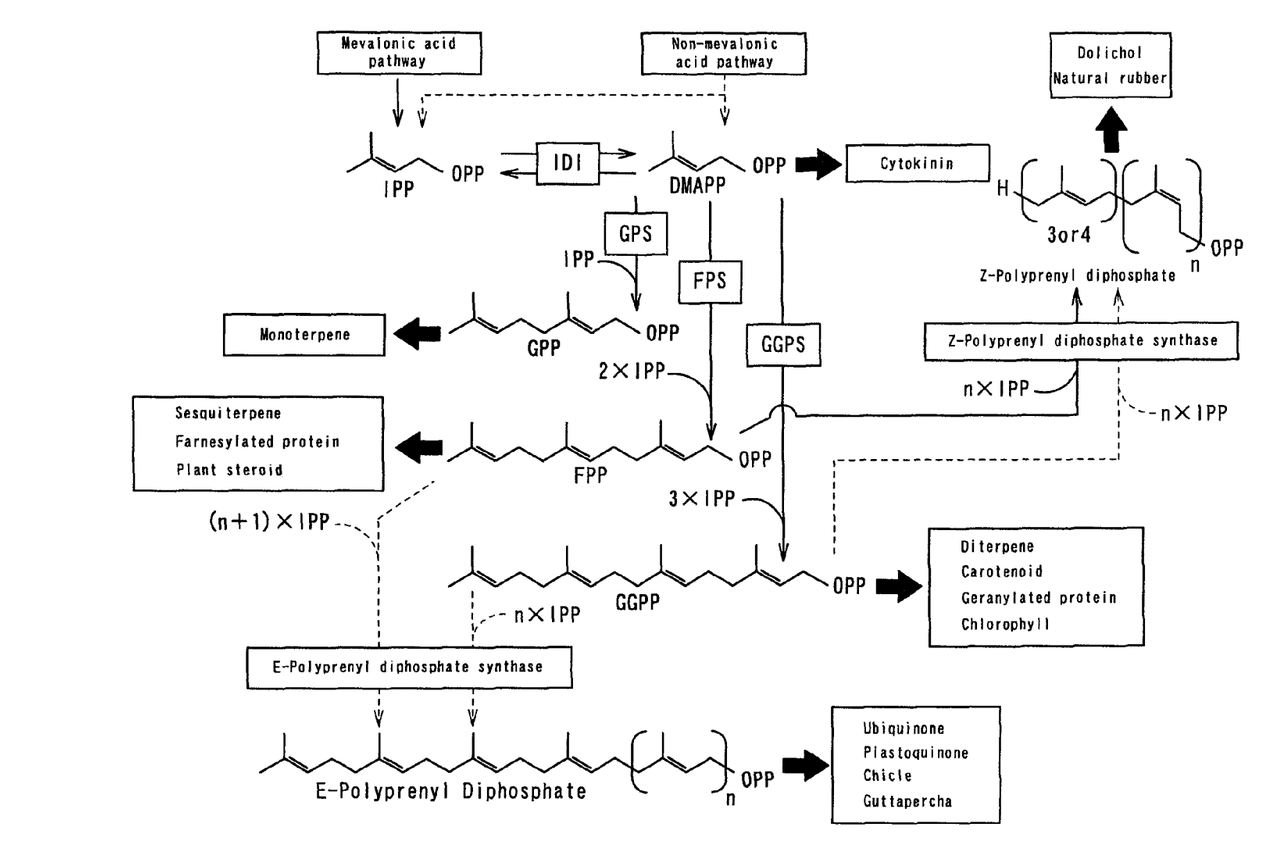
FIG. 1 is a FIGURE showing isoprenoid diphosphates which are produced by various kinds of prenyl transferases.

Prenyl transferase means a cluster of enzymes that synthesizes variety of isoprenyl diphosphates such as geranyl diphosphate (GPP: C10), farnesyl diphosphate (FPP: C15), geranylgeranyl diphosphate (GGPP: C20), geranyl feranyl diphosphate (GFPP: 25) and hexaprenyl diphosphate. The prenyl transferase serves as basic precursor of various terpenoids by ligating isoprene unit, and located in the mainstream of terpenepenoid biosynthesis. Isoprenyl diphosphates that are produced by various prenyl trabsferases are shown in FIG. 1. As mentioned above, prenyl transferase according to the present specification comprehensively indicate enzymes catalyzing the reaction of adding one isoprene unit and includes all enzymes such as geranyl diphosphate synthase, farnesyl disphosphate syshtetase, geranylgeranyl diphosphate synthase, geranyl farnesyl disphosphate synthase and hexaprenyl disphosphate synthase.

SUMMARY OF THE INVENTION

The analysis in regard to the gene cluster of prenyl transferase from *Hevea brasiliensis* has not been sufficient yet. The object of the invention is to isolate the gene cluster of prenyl transferase from *Hevea brasiliensis* and to analyze nucleotide sequences of the respective genes constituting the above gene cluster.

The sequence assumed to be included in the gene cluster of prenyl transferase is specified by a syntactic analysis of the information on the gene fragments obtained by EST (Expression Sequence Tags) analysis of *Hevea brasiliensis* and the information on the known gene database, and said gene homolog is obtained by cloning full length cDNA.

The gene cluster of the present invention encoding prenyl transferases is a gene cluster encoding a group of enzymes involved in the biosynthesis of isoprene backbone of natural rubber. Therefore, practical use plants which produce a large amount of natural rubber can be produced by transformation of plants, especially rubber-producing plants, by the gene cluster obtained in the present invention. More specifically, it can be expected to increase the amount of production of natural rubber by producing transformed *Hevea brasiliensis* by introducing the gene cluster of the present invention. Now herein, "to improve productivity of rubber" means to increase the amount of rubber production by introducing the prenyl transeferase gene of the present invention.

BEST MODE FOR CARRYING OUT THE INVENTION

Total RNA was extracted from latex of the standard tree and xylem of the current year branch of *Hevea brasiliensis* so as to prepare cDNA libraries. Exhaustive one-pass sequence analysis was performed on these libraries. Then 16407 EST sequences were obtained from the cDNA library prepared from the latex and 16305 EST sequences from the cDNA library were obtained from the xylem with high accuracy (Total 32442). On the obtained partial sequences, clustering analysis based on similarity between sequences and annotation analysis based on comparison with known genes were performed, and thus an EST database of *Hevea brasiliensis* was constructed.

In the obtained EST database, the inventors have found EST sequences which are assumed to encode geranyl diphosphate synthase and geranyl geranyl diphosphate synthase. As to these sequences, the inventors have determined the 3'terminal sequence by 3'-RACE (Rapid Amplification of cDNA Ends) and obtained full-length cDNAs.

A gene coding geranyl diphosphate synthase is represented by nucleotide numbers from 1 to 1074 in SEQ ID NO:1 in the sequence list. The part corresponding to nucleotide numbers from 126 to 1043 in the nucleotide sequence in SEQ ID NO:1 in the sequence list corresponds to the open reading frame. A deduced amino acid sequence of geranyl diphosphate synthase obtained from the nucleotide sequence of the reading frame is represented by amino acid numbers from 1 to 306 in SEQ ID NO:2 in the sequence list. Meanwhile, geranyl diphosphate synthase is an enzyme that catalyzes the reaction which biosynthesizes geranyl diphosphate using isopentenyl diphosphate and dimethylallyl diphosphate as substrate.

A gene encoding geranylgeranyl diphosphate synthase is represented by nucleotide numbers from 1 to 1662 in SEQ ID NO:3 in the sequence list. The part corresponding to nucleotide numbers from 181 to 1098 in the nucleotide sequence list in SEQ ID NO:3 in the sequence list corresponds to the open reading frame. A deduced amino acid sequence of geranylgeranyl diphosphate synthase obtained from the nucleotide sequence of the reading frame is represented by amino acid numbers from 1 to 306 in SEQ ID NO:4 in the sequence list. Meanwhile, geranylgeranyl diphosphte synthase is an enzyme that catalyzes the reaction which biosynthesizes geranylgeranyl diphosphate using isopentenyl diphosphate and dimethylallyl diphosphate as substrate.

A gene encoding geranylgeranyl diphosphate obtained from another clone is represented by nucleotide numbers from 1 to 1278 in SEQ ID NO:5 in the sequence list. The part corresponding to nucleotide numbers from 54 to 1043 in the nucleotide sequence in SEQ ID NO:5 in the sequence list corresponds to the open reading frame. A deduced amino acid sequence of geranylgeranyl diphosphate synthase obtained from the nucleotide sequence of the reading frame is represented by amino acid numbers from 1 to 330 in SEQ ID NO:6 in the sequence list. Meanwhile, geranylgeranyl diphosphate synthase is an enzyme that catalyzes the reaction which biosynthesizes geranylgeranyl diphosphate using isopentenyl diphosphate and dimethylallyl diphosphate as substrate.

A gene encoding geranylgeranyl diphosphate synthase obtained from another clone is represented by nucleotide numbers from 1 to 1181 in SEQ ID NO:7 in the sequence list. The part corresponding to nucleotide numbers from 54 to 1037 in the nucleotide sequence in SEQ ID NO:7 in the sequence list corresponds to the open reading frame. A deduced amino acid sequence of geranylgeranyl diphosphate synthase obtained from the nucleotide sequence of the reading frame is represented by amino acid numbers from 1 to 328 in SEQ ID NO:8 in the sequence list. Meanwhile, geranylgeranyl diphosphate synthase is an enzyme that catalyzes the reaction which biosynthesizes geranylgeranyl diphosphte using isopentenyl diphosphate and dimethylallyl diphosphate as substrate.

According to recombinant DNA techniques, artificial mutation can be made to a particular site of the original DNA, without changing the fundamental properties of the DNA or in such a way as to improve these properties. As to genes having natural nucleotide sequences provided according to the present invention or even genes having nucleotide sequences different from the natural sequence, artificial insertion, deletion and substitution can be performed in the same manner, and they can be altered to have an equal or improved properties as the natural genes. Moreover, the present invention includes such mutated genes.

More specifically, a gene consisting of a nucleotide sequence in which a part of the nucleotide sequence shown in SEQ ID NO:1 in the sequence list has been deleted, substituted or added means a gene in which no more than 20, preferably no more than 10, more preferably no more than 5 nucleotides in the nucleotide sequence in SEQ ID NO:1 have been substituted. Further, such a gene has no less than 95%, preferably no less than 97%, more preferably no less than 99% homology with the nucleotide sequence shown in SEQ ID NO:1. Even such a gene is also within the scope of the present invention, as long as the gene encodes a protein having the functions as geranyl diphosphate synthase, which biosynthesizes geranyl diphosphate using isopentenyl diphosphate and dimethylallyl diphosphate as substrate. Additionally, such a gene hybridizes with the gene shown in SEQ ID NO:1 under stringent conditions.

Similarly, a gene consisting of a nucleotide sequence in which a part of the nucleotide sequence shown in SEQ ID NO:3 in the sequence list has been deleted, substituted or added means a gene in which no more than 20, preferably no more than 10, more preferably no more than 5 nucleotides in the nucleotide sequence in SEQ ID NO:3 have been substituted. Further, such a gene has no less than 95%, preferably no less than 97%, more preferably no less than 99% homology with the nucleotide sequence shown in SEQ ID NO:3. Even such a gene is also within the scope of the present invention, as long as the gene encodes a protein having the functions as geranylgeranyl diphosphate synthase, which biosynthesizes geranylgeranyl diphosphate using isopentenyl diphosphate and dimethylallyl diphosphate as substrate. Additionally, such a gene hybridizes with the gene shown in SEQ ID NO:3 under stringent conditions.

Similarly, a gene consisting of a nucleotide sequence in which a part of the nucleotide sequence shown in SEQ ID NO:5 in the sequence list has been deleted, substituted or added means a gene in which no more than 20, preferably no more than 10, more preferably no more than 5 nucleotides in the nucleotide sequence in SEQ ID NO:5 have been substituted. Further, such a gene has no less than 95%, preferably no less than 97%, more preferably no less than 99% homology with the nucleotide sequence shown in SEQ ID NO:5. Even such a gene is also within the scope of the present invention, as long as the gene encodes a protein having the functions as geranylgeranyl diphosphate synthase, which biosynthesizes geranylgeranyl diphosphate using isopentenyl diphosphate and dimethylallyl diphosphate as substrate. Additionally, such a gene hybridizes with the gene shown in SEQ ID NO:5 under stringent conditions.

Similarly, a gene consisting of a nucleotide sequence in which a part of the nucleotide sequence shown in SEQ ID NO:7 in the sequence list has been deleted, substituted or added means a gene in which no more than 20, preferably no more than 10, more preferably no more than 5 nucleotides in the nucleotide sequence in SEQ ID NO:7 are substituted. Further, such a gene has no less than 95%, preferably no less than 97%, more preferably no less than 99% homology with the nucleotide sequence shown in SEQ ID NO:7. Even such a gene is also within the scope of the present invention, as long as the gene encodes a protein having the functions as geranylgeranyl diphosphate synthase, which biosynthesizes geranylgeranyl diphosphate using isopentenyl diphosphate and dimethylallyl diphosphate as substrate. Additionally, such a gene hybridizes with the gene shown in SEQ ID NO:7 under stringent conditions.

Those skilled in the art may select conditions for hybridization ad libitum. A membrane onto which a DNA or RNA molecule to be tested has been transferred and a labeled probe can be hybridized in an applicable hybridization buffer. The hybridization buffer may be composed of 5×SSC, 0.1 weight % N-lauroyl sarcosine, 0.02 weight % SDS, 2 weight % blocking reagent for nucleotide hybridization, and 50 weight % formamide, for instance. As the blocking reagent for nucleotide hybridization, for example, commercially available blocking reagent for nucleotide hybridization can be dissolved into a buffer solution (pH 7.5) composed of 0.1 M maleic acid and 0.15 M NaCl to make the concentration of the blocking reagent to be 10%. 20×SSC may be composed of 3M NaCl and 0.3M citric acid solution. SSC may be used preferably at 3 to 6×SSC concentration, and more preferably at 4 to 5×SSC concentration.

Hybridization may be performed at 40 to 80° C., preferably at 50 to 70° C., and more preferably at 55 o 65° C. Washing may be performed using a washing buffer after incubation for several hours or overnight. Washing may be performed preferably at room temperature, and more preferably at the temperature of hybridization. The washing buffer may be composed of 6×SSC+0.1 weight % SDS solution, preferably composed of 4×SSC+0.1 weight % SDS solution, more preferably composed of 2×SSC+0.1 weight % SDS solution, even more preferably composed of 1×SSC+0.1 weight % SDS solution, and most preferably composed of 0.1×SSC+0.1 weight % SDS solution. The membrane can be washed with such a washing buffer and the DNA molecule or RNA molecule hybridized with the probe can be identified by the label used for the probe.

Further herein, a protein consisting of an amino acid sequence in which a part of the amino acid sequence shown in SEQ ID NO:2 has been deleted, substituted or added means a protein in which no more than 20, preferably no more than 10, more preferably no more than 5 amino acids in the amino acid sequence in SEQ ID NO:2 have been substituted. Further, such a protein has no less than 95%, preferably no less than 97%, more preferably no less than 99% homology with the amino acid sequence shown in SEQ ID NO:2. Even such a protein is within the scope of the present invention, as long as the protein has the functions as geranyl diphosphate synthase, which biosynthesizes geranyl diphosphate using isopentenyl diphosphate and dimethylallyl diphosphate as substrate.

Similarly, a protein consisting of an amino acid sequence in which a part of the amino acid sequence shown in SEQ ID NO:4 in the sequence list has been deleted, substituted or added means a protein in which no more than 20, preferably no more than 10, more preferably no more than 5 amino acids in the amino acid sequence in SEQ ID NO:4 have been substituted. Further, such a protein has no less than 95%, preferably no less than 97%, more preferably no less than 99% homology with the amino acid sequence shown in SEQ ID NO:4. Even such a protein is within the scope of the present invention, as long as the protein has the functions as geranylgeranyl diphosphate synthase, which biosynthesizes geranylgeranyl diphosphate using isopentenyl diphosphate and dimethylallyl diphosphate as substrate.

Similarly, a protein consisting of an amino acid sequence in which a part of the amino acid sequence shown in SEQ ID NO:6 in the sequence list has been deleted, substituted or added means a protein in which no more than 20, preferably no more than 10, more preferably no more than 5 amino acids in the amino acid sequence in SEQ ID NO:6 have been substituted. Further, such a protein has no less than 95%, preferably no less than 97%, more preferably no less than 99% homology with the amino acid sequence shown in SEQ ID NO:6. Even such a protein is within the scope of the present invention, as long as the protein has the functions as geranylgeranyl diphosphate synthase, which biosynthesizes geranylgeranyl diphosphate using isopentenyl diphosphate and dimethylallyl diphosphate as substrate.

Similarly, a protein consisting of an amino acid sequence in which a part of the amino acid sequence shown in SEQ ID NO:8 in the sequence list has been deleted, substituted or added means a protein in which no more than 20, preferably no more than 10, more preferably no more than 5 amino acids in the amino acid sequence in SEQ ID NO:8 have been substituted. Further, such a protein has no less than 95%, preferably no less than 97%, more preferably no less than 99% homology with the amino acid sequence shown in SEQ ID NO:8. Even such a protein is within the scope of the present invention, as long as the protein has the functions as geranylgeranyl diphosphate synthase, which biosynthesizes geranylgeranyl diphosphate using isopentenyl diphosphate and dimethylallyl diphosphate as substrate.

The gene cluster of the present invention encoding prenyl transferase can be introduced into such plants as rubber tree to enhance its expression, so that the expression level of gene products of prenyl transferase can be increased in said plants. The pathway, in which various prenyl transferases are involved, is known to be involved in the production of natural rubber by catalyzing the reaction of adding isoprene backbone of natural rubber. Therefore, increase in the amount of rubber production in a rubber tree can be expected by producing said rubber tree transformed by the prenyl transferase gene.

The plant to be introduced with gene of the present invention is not limited to *Hevea brasiliensis*, the examples of other plants may be guayule, cassava, sunflower, lettuce, Indian rubber tree, and etc., but the target plants to be transformed are not limited to these plants, and transformants into which the gene of the present invention has been introduced can be produced in various plants. Particularly, according to this invention, it is preferable to transform rubber-producing plants, such as *Hevea brasiliensis*, in order to improve the quality of the rubber obtained from said rubber-producing plants. Rubber-producing plants are known to spread wide variety of families including Asteraceae, Moraceae, Euphorbiaceae, Asclepiadaceae, and Apocynaceae.

As a method for producing transformants, usual methods known in the art can be used. As an useful promoter for activating the introduced gene, the cauliflower mosaic virus 35S promoter widely used in the art, for example, can be used and positioned upstream of the gene of the present invention, which is to be transduced. In many cases, some promoter is required to achieve sufficient expression of the introduced foreign gene. The preferred promoter is not limited to the cauliflower mosaic virus 35S promoter, and various promoters widely used in the art may also be used. In addition, promoter specific for latex duct is preferably used in order to increase production of rubber.

Furthermore, the vectors which can be used in the present invention may include, but not limited to, vectors such as pIG121-Hm, pBI12, pBI221, pBIN19, pCC22, pGA482, pPCV001, pCGN1547, pJJ1881, pPZP111, pGreen0029, pBI101, pBI121, and pYLTAC7. Transgenic plants can be prepared by introducing such vectors into *Agrobacterium*, for instance, to have a callus or a plantlet infected, and thus seeds derived from such transgenic plants can be obtained. Further, the transformation method for introducing the plant gene of the present invention into plants is not limited to the *Agrobacterium* method, but various methods commonly used in the art including the particle gun method and the electroporation method may also be used. Additionally, an example in which a foreign gene is introduced into rubber tree for transformation is disclosed in Japanese Patent Publication No. 1996-116977. Therefore, those skilled in the art can produce a transgenic plant, into which the gene of the present invention has been introduced, by making appropriate alterations with reference to the description of Japanese Patent Publication No. 1996-116977.

EXAMPLES (Materials)

Latex and xylem from the current year branch of *Hevea brasiliensis* standard tree PRIM 600 cultivated in Cikampek, Indonesia were used as a plant sample. The latex was suspended in an equal amount of 2× sampling buffer (0.1M Tris-HCL, 0.3M LiCl, 0.01M EDTA, 10% SDS) immediately after sampling the latex. Also, YKO Heterozygous Essential Strain Collection-Glycerol Stocks (Open Biosystems, Inc) offered commercially was used as a mutant yeast strain.

(RNA Extraction from *Hevea brasiliensis*)

RNA was extracted from the latex and xylem respectively by the following procedures. Immediately after sampling, the sample (equivalent to 25 ml of latex) suspended in an equal amount of 2× sampling buffer (0.1M Tris-HCL, 0.3M LiCl, 0.01M EDTA, 10% SDS) was centrifuged, and the upper layer constituting the rubber layer was removed. Then, 1.5 equivalent amount of 2×CTAB solution (2% Hexadecyltrimethylammonium bromide(CTAB), 1% 2-mercaptoethanol, 0.1 M Tris-HCL (pH9.5), 1.4 M NaCl, 20 mM EDTA) was added. After incubating at 65° C. for 10 minutes, treatment with chloroform/isoamyl alcohol was performed (repeated twice). A ¼ amount of 10 M LiCl was added to the collected aqueous layer and mixed, then incubated at −20° C. for 2 hours (selective precipitation of RNA). It was centrifuged, the precipitation was dissolved into an appropriate amount of TE, then centrifuged, and the supernatant was collected (polysaccharides were removed). Further, the fraction was treated with phenol, phenol/chloroform, chloroform/isoamyl alcohol, and then selective precipitation of RNA by LiCl was performed again. The precipitation was cleaned with 70% ethanol, and dissolved in DEPC-treated water after being dried under reduced pressure. Thus, total RNA derived from latex was obtained.

Also, the phloem of the current year branch was peeled off by a knife to obtain about 1 g of xylem, and it was pound in a mortar with a pestle while cooling with liquid nitrogen. The total RNA derived from xylem was obtained using RNeasy Plant Mini Kit (registered trademark, Qiagen).

The obtained RNA solution was quantified by optical density measurements, and this was confirmed by electrophoresis. A 450 μg of RNA was obtained from 25 mg of latex, and 110 μg of RNA was obtained from 1 g of xylem.

(Preparation of cDNA Libraries of *Hevea brasiliensis*)

The cDNA libraries were prepared from the RNA samples derived from *Hevea brasiliensis* latex and xylem by the G-Capping method at Hitachi Instruments Service Co., Ltd. The G-Capping method is a method that can achieve full-length cDNAs at a high percentage.

The cDNA library derived from the latex has the library size of $1.7 \times 10^5$, the insert percentage of 71% (24 samples/agarose gel electrophoresis), and the percentage of full-length cDNA was 82% (toward clones with insert). The size of cDNA library derived from the xylem was $2.9 \times 10^5$, and the percentage of insert was 80% (24 samples/agarose gel electrophoresis), and the percentage of full-length cDNA was 87% (toward clones with insert).

(Sequence Analysis, Clustering Analysis and Annotation Analysis of EST Sequences)

At the Genome Information Science Laboratory of Kitasato Institute for Life Sciences of Kitasato University, exhaustive one-pass sequence analysis was performed on approximately 20,000 clones of the cDNA libraries derived from latex and xylem of *Hevea brasiliensis* respectively. According to the sequence information obtained from the sequence analysis, clones with no insert and clones failed to determine sequence were removed, thereby high accuracy sequence information was obtained. The latex cDNA library and xylem cDNA library provided 16407 EST sequences and 16305 EST sequences respectively with high accuracy (total 32442).

The obtained partial sequences were subjected to clustering analysis based on similarity between sequences, and annotation analysis based on comparison with known genes, thereby an EST database of *Hevea brasiliensis* was constructed. A VISUALBIO clustering of NTT Software was used for the clustering analysis. The annotation analysis was performed by homology search using NCBI BLAST. The database used for the search was nr (All non-redundant GenBank CDS translations+PDB+SwissProt+PIR (Peptide Sequence Database)).

In the obtained EST database, EST sequences which are assumed to encode prenyl diphosphate synthase and prenylprenyl diphosphate synthase were found.

(Determination of Sequences at the 3' Terminal by 3'-RACE)

The sequences at the 3' terminal were determined by 3'-RACE (Rapid Amplification of cDNA Ends) on each sequences obtained by the analyses above to obtain full-length cDNAs. For 3'-RACE, a 3'-Full RACE Core Set (Takara Bio Inc.) was used. An oligo-dT primer was used for reverse transcription. For amplification by PCR, an oligo-dT primer and a sense primer having sequence identity with a part of known sequences were used. The amplified fragments were obtained from reverse transcription and PCR, then the fragments were subjected to TA cloning into pT7Blue vector, which was succeeded by sequence analysis.

The sequences obtained in this way are as follows; (1) the nucleotide sequence of the gene of geranyl diphosphate synthase (SEQ ID NO:1 in the sequence list), (2) the nucleotide sequence of the gene of geranylgeranyl diphosphate synthase (SEQ ID NO:3 in the sequence list), (3) the nucleotide sequence of the gene of geranylgeranyl diphosphate synthase derived from another clone (SEQ ID NO:5 in the sequence list), and (4) the nucleotide sequence of the gene of geranylgeranyl diphosphate synthase derived from another clone (SEQ ID NO:7 in the sequence list).

Additionally, the deduced amino acid sequences of the proteins obtained from the open reading frames of these nucleotide sequences are as follows; (1) the amino acid sequence of geranyl diphosphate synthase (SEQ ID NO:2 in the sequence list), (2) the amino acid sequence of geranylgeranyl diphosphate synthase (SEQ ID NO:4 in the sequence list), (3) the amino acid sequence of geranylgeranyl diphosphate synthase derived from another clone (SEQ ID NO:6 in the sequence list), and (4) the amino acid sequence of geranylgeranyl diphosphate synthase derived from another clone (SEQ ID NO:8 in the sequence list.

(Functional Confirmation by Enzymatic Activity)

Among the sequences obtained by the above-mentioned procedure, as to the candidate gene of geranylgeranyl diphosphate synthase shown in SEQ ID NO:3 the inventors produced recombinant protein from the gene, conducted enzymatic reaction using the recombinant protein, and analyzed on the reaction product to confirm the function of the gene.

At first, the candidate gene of geranylgeranyl diphosphate synthase from *Hevea brasiliensis* was inframe inserted into pColdI vector (Takara) to produce an expression plasmid. Meanwhile, various commercially available expression plasmids other than the pColdI vector such as pGEX, pET can be also utilized as an expression plasmid. The *E. coli* BL21 (DE3) strain was transformed by the expression plasmid, and the transformants were selected in a selection medium plate containing ampicillin. Meanwhile, as the *E. coli* strain to be used for the expression of the recombinant protein, various *E. coli* strains which are commercially available can be used, for example, Origami, Rosetta and Rosetta-gami (Novagen). The transformed *E. coli* was transplanted onto a LB agar medium containing 50 μg ampicillin, and cultured at 37° C. with shaking. The culture medium was cooled to 15° C. when the value of OD600 reached to 0.4, then it was left for 30 min. IPTG was added to reach the final concentration of 0.1 mM, and it was further incubated with shaking for 24 hours at 15° C. Meanwhile, the conditions for induction such as the temperature of culture and the concentration of IPTG can be altered in various ways. After the incubation, the cell bodies were harvested and disrupted, to obtain the recombinant protein.

Otherwise, the candidate gene of geranylgeranyl diphosphate synthase from *Hevea brasiliensis* was inframe inserted into pVL1393 transfer vector (Takara) for protein expression using insect baculovirus system, to produce an expression plasmid. Meanwhile, not only the pVL1393 vector, but also various commercially available transfer vectors such as pAcAB3 can be also used. The baculovirus of $2.5 \times 10^6$ cells, such as Sf-9, was seeded onto a 25 cm² flask for cell culture, and it was settled for 30 minutes at room temperature. After confirmed that the cells were attached to the flask, the medium was changed by 1 ml of serum-free medium. The Sf-9 cell was transfected with the transfer vector inserted with the candidate gene of geranylgeranyl diphosphate synthase and the baculovirus genomic DNA, using the lipofection method. The DNA was absorbed to the cells for 1 hour at room temperature with shaking periodically, 5 ml of medium containing 5% fetal bovine serum was added, and cultured at 28° C. for 4 days. After completion of the culture, the supernatant containing virus was recovered, and used as a virus stock. For the virus stock contained non-transformants as well, it was purified by plaque assay. The Sf-9 cell ($2.5 \times 10^6$ cells) was infected with the purified recombinant virus, and then it was cultured in a suspension for 72 hours at 28° C. After completion of the cell culture, cells were recovered and disrupted to obtain the soluble recombinant protein.

Using the soluble protein thus obtained, the enzymatic activity of geranylgeranyl diphosphate synthase was determined using the method described in a literature (Oh, (2000) J. Plant Physiology, 157, p 535). In concrete, an appropriate amount of the soluble recombinant protein was added into a reaction solution containing 50 mM phosphate Buffer (pH7.4) 5 mM $MgCl_2$, 5 mM KF, 5 mM iodoacetamide, 0.1% (w/v) Triton X-100, 10 µM $^{14}$C-IPP and 5 µM FPP, then it was reacted for 4 hours at 30° C.

The reaction product was extracted by butanol, it was incubated overnight at 37° C. for hydrolysis using potato acid phosphatase (Sigma) thereafter. The hydrolyzed reaction product was extracted with hexane, which was developed on reversed phase TLC plate using a developing solvent consisting of acetone:$H_2O$=9:1. The TLC plate was exposed to an imaging plate, and the radioactivity was analyzed using BAS1500 imaging analyzer (Fuji). The radio-active reaction products were identified by comparison with standard samples which were visualized with iodine (such as farnesol, geranylgeraniol).

The recombinant protein of the candidate gene was expressed as described above, the activity as a prenyl transferase was determined using $^{14}$C-labeled IPP, the reaction product was further analyzed, thereby the inventors tried to identify the function of the gene shown in SEQ ID NO: 3. As the this result, among the EST sequences derived from *Hevea brasiliensis*, as to the gene of geranylgeranyl diphosphate synthase shown in SEQ ID NO:3, the function of the gene could be identified using the enzymatic activity.

INDUSTRIAL AVAILABILITY

According to the present invention, a gene cluster encoding various kinds of prenyl transferase of *Hevea brasiliensis* was obtained, and the nucleotide sequences of these genes were determined. The prenyl transferases are involved in the biosynthesis of isoprene backbone of natural rubber. Therefore, improvement of productivity of rubber can be expected, by transforming plants by the gene cluster obtained in the present invention.

The invention claimed is:

1. An isolated protein consisting of the amino acid sequence of SEQ ID NO:4.

2. An isolated gene encoding the polypeptide according to claim 1.

3. An isolated gene consisting of the nucleotide sequence of nucleotide 181 to 1098 of SEQ ID NO:3.

4. An isolated gene consisting of the nucleotide sequence of nucleotide 1 to 1662 of SEQ ID NO:3.

5. A transgenic plant, wherein the productivity of rubber in the plant is improved by introducing the gene according to any one of claims 2 to 4 into said plant.

6. A method to improve the productivity of rubber in a plant, the method comprising transforming said plant with the gene according to any one of claims 2 to 4.

* * * * *